(12) United States Patent
Miesel et al.

(10) Patent No.: US 8,489,196 B2
(45) Date of Patent: Jul. 16, 2013

(54) SYSTEM, APPARATUS AND METHOD FOR INTERACTING WITH A TARGETED TISSUE OF A PATIENT

(75) Inventors: Keith Alan Miesel, St. Paul, MN (US); Sudha Nagavarapu, St. Paul, MN (US); Randall Maas, Chaska, MN (US)

(73) Assignee: Medtronic, Inc., Minneapolis, MN (US)

( * ) Notice: Subject to any disclaimer, the term of this patent is extended or adjusted under 35 U.S.C. 154(b) by 387 days.

(21) Appl. No.: 10/678,402

(22) Filed: Oct. 3, 2003

(65) Prior Publication Data
US 2005/0075683 A1    Apr. 7, 2005

(51) Int. Cl.
*A61N 1/36* (2006.01)
(52) U.S. Cl.
USPC ............... 607/60; 607/36; 607/53; 607/54
(58) Field of Classification Search
USPC .................................. 607/60, 36, 53, 54
See application file for complete search history.

(56) References Cited

U.S. PATENT DOCUMENTS

| | | | |
|---|---|---|---|
| 4,595,009 A | 6/1986 | Leinders | |
| 4,791,935 A | 12/1988 | Baudino et al. | |
| 4,886,064 A | 12/1989 | Strandberg | |
| 5,148,265 A | 9/1992 | Khandros et al. | |
| 5,148,266 A | 9/1992 | Khandros et al. | |
| 5,178,161 A | 1/1993 | Kovacs | |
| 5,258,330 A | 11/1993 | Khandros et al. | |
| 5,275,171 A | 1/1994 | Barcel | |
| 5,280,413 A | 1/1994 | Pai | |
| 5,281,219 A | 1/1994 | Kallok | |
| 5,314,495 A | 5/1994 | Kovacs | |
| 5,325,870 A | 7/1994 | Kroll et al. | |
| 5,336,253 A | 8/1994 | Gordon et al. | |
| 5,346,861 A | 9/1994 | Khandros et al. | |
| 5,347,159 A | 9/1994 | Khandros et al. | |
| 5,402,494 A | 3/1995 | Flippe et al. | |
| 5,411,532 A | 5/1995 | Mortazavi | |
| 5,423,873 A * | 6/1995 | Neubauer et al. ............... | 607/68 |

(Continued)

FOREIGN PATENT DOCUMENTS

| EP | 0317986 | 5/1989 |
|---|---|---|
| EP | 0487413 | 5/1992 |

(Continued)

OTHER PUBLICATIONS

WO 2003041795, May 22, 2003, Stypulkowski.

(Continued)

*Primary Examiner* — Niketa Patel
*Assistant Examiner* — Alyssa M Alter (57) ABSTRACT

A method and an apparatus are provided for interacting with targeted tissue of a patient. The apparatus comprises a central control module, a satellite module, and a lead. The satellite module comprises a processor, a communication module, a switching module, a memory, a sense amp, and a A/D converter. The apparatus is adapted for subcutaneous implantation. The central control module is coupled to the satellite module. The lead is coupled to the satellite module. A programming word comprising information to be sent to the satellite module is provided. The programming word is converted into identifiable groups of pulses corresponding to bits of the programming word. The identifiable groups of pulses are sent to the satellite module. The identifiable groups of pulses are converted to information for providing a therapy to the patient. The energy from the identifiable groups of pulses is stored to power the satellite module.

9 Claims, 5 Drawing Sheets

U.S. PATENT DOCUMENTS

| | | | |
|---|---|---|---|
| 5,470,345 A | 11/1995 | Hassler et al. | |
| 5,501,703 A | 3/1996 | Holsheimer et al. | |
| 5,513,793 A | 5/1996 | Malmgren | |
| 5,571,156 A | 11/1996 | Schmukler | |
| 5,593,430 A | 1/1997 | Renger | |
| 5,620,476 A | 4/1997 | Truex et al. | |
| 5,643,330 A | 7/1997 | Holsheimer et al. | |
| 5,679,977 A | 10/1997 | Khandros et al. | |
| 5,682,061 A | 10/1997 | Khandros et al. | |
| 5,683,435 A | 11/1997 | Truex et al. | |
| 5,685,885 A | 11/1997 | Khandros et al. | |
| 5,738,270 A | 4/1998 | Malmgren | |
| 5,782,891 A | 7/1998 | Hassler et al. | |
| 5,814,089 A * | 9/1998 | Stokes et al. | 607/32 |
| 5,843,135 A | 12/1998 | Weijand et al. | |
| 5,848,467 A | 12/1998 | Khandros et al. | |
| 5,852,326 A | 12/1998 | Khandros et al. | |
| 5,902,326 A | 5/1999 | Lessar et al. | |
| 5,925,070 A | 7/1999 | King et al. | |
| 5,935,155 A | 8/1999 | Humayun et al. | |
| 5,950,304 A | 9/1999 | Khandros et al. | |
| 5,999,848 A * | 12/1999 | Gord et al. | 607/2 |
| 6,011,993 A | 1/2000 | Tziviskos et al. | |
| 6,038,480 A | 3/2000 | Hrdlicka et al. | |
| 6,052,623 A | 4/2000 | Fenner et al. | |
| 6,058,331 A * | 5/2000 | King | 607/62 |
| 6,083,252 A | 7/2000 | King et al. | |
| 6,125,290 A | 9/2000 | Miesel | |
| 6,125,291 A | 9/2000 | Miesel et al. | |
| 6,133,627 A | 10/2000 | Khandros et al. | |
| 6,134,459 A | 10/2000 | Roberts et al. | |
| 6,141,588 A * | 10/2000 | Cox et al. | 607/9 |
| 6,144,866 A | 11/2000 | Miesel et al. | |
| 6,163,723 A | 12/2000 | Roberts et al. | |
| 6,164,284 A | 12/2000 | Schulman et al. | |
| 6,198,952 B1 | 3/2001 | Miesel | |
| 6,248,080 B1 * | 6/2001 | Miesel et al. | 600/561 |
| 6,372,527 B1 | 4/2002 | Khandros et al. | |
| 6,392,306 B1 | 5/2002 | Khandros et al. | |
| 6,411,854 B1 | 6/2002 | Tziviskos et al. | |
| 6,414,835 B1 | 7/2002 | Wolf et al. | |
| 6,418,348 B1 | 7/2002 | Witte | |
| 6,421,566 B1 | 7/2002 | Holsheimer | |
| 6,465,893 B1 | 10/2002 | Khandros et al. | |
| 6,473,653 B1 | 10/2002 | Schallhorn et al. | |
| 6,516,227 B1 * | 2/2003 | Meadows et al. | 607/46 |
| 6,564,807 B1 | 5/2003 | Schulman et al. | |
| 6,829,509 B1 | 12/2004 | MacDonald et al. | |
| 7,286,878 B2 * | 10/2007 | Stypulkowski | 607/37 |
| 2001/0001125 A1 | 5/2001 | Schulman et al. | |
| 2001/0030370 A1 | 10/2001 | Khandros et al. | |
| 2002/0011663 A1 | 1/2002 | Khandros et al. | |
| 2002/0052563 A1 | 5/2002 | Penn et al. | |
| 2002/0116028 A1 | 8/2002 | Greatbatch et al. | |
| 2002/0116029 A1 | 8/2002 | Miller et al. | |
| 2002/0116033 A1 | 8/2002 | Greatbatch et al. | |
| 2002/0116034 A1 | 8/2002 | Miller et al. | |
| 2002/0128689 A1 | 9/2002 | Connelly et al. | |
| 2002/0128691 A1 | 9/2002 | Connelly | |
| 2002/0128694 A1 | 9/2002 | Holsheimer | |
| 2002/0133086 A1 | 9/2002 | Connelly et al. | |
| 2002/0133199 A1 | 9/2002 | MacDonald et al. | |
| 2002/0133200 A1 | 9/2002 | Weiner et al. | |
| 2002/0133201 A1 | 9/2002 | Connelly et al. | |
| 2002/0133202 A1 | 9/2002 | Connelly et al. | |
| 2002/0133208 A1 | 9/2002 | Connelly | |
| 2002/0133211 A1 | 9/2002 | Weiner et al. | |
| 2002/0133216 A1 | 9/2002 | Connelly et al. | |
| 2002/0138102 A1 | 9/2002 | Weiner et al. | |
| 2002/0138107 A1 | 9/2002 | Weiner et al. | |
| 2002/0138108 A1 | 9/2002 | Weiner et al. | |
| 2002/0138110 A1 | 9/2002 | Connelly et al. | |
| 2002/0138112 A1 | 9/2002 | Connelly et al. | |
| 2002/0138113 A1 | 9/2002 | Connelly et al. | |
| 2002/0138124 A1 | 9/2002 | Helfer et al. | |
| 2002/0143258 A1 | 10/2002 | Weiner et al. | |
| 2002/0147470 A1 | 10/2002 | Weiner et al. | |
| 2002/0155728 A1 | 10/2002 | Khandros et al. | |
| 2002/0183796 A1 | 12/2002 | Connelly | |
| 2002/0198569 A1 | 12/2002 | Foster et al. | |
| 2002/0198604 A1 | 12/2002 | Schulman et al. | |
| 2003/0093130 A1 | 5/2003 | Stypulkowski | |
| 2003/0139783 A1 | 7/2003 | Hill | |
| 2003/0168253 A1 | 9/2003 | Khandros et al. | |
| 2004/0011366 A1 | 1/2004 | Schulman et al. | |
| 2004/0103906 A1 | 6/2004 | Schulman et al. | |

FOREIGN PATENT DOCUMENTS

| | | |
|---|---|---|
| EP | 1111672 | 6/2001 |
| EP | 0 844 899 B1 | 7/2003 |
| EP | 1353374 | 10/2003 |
| GB | 2 124 495 A | 2/1984 |
| GB | 2 134 335 A | 8/1984 |
| GB | 2 166 606 A | 10/1985 |
| WO | WO 92/05582 | 4/1992 |
| WO | WO95 19804 A1 | 7/1995 |
| WO | WO97 06853 A1 | 2/1997 |
| WO | WO97 20332 A1 | 6/1997 |
| WO | WO97 38752 A2 | 10/1997 |
| WO | WO97 38752 A3 | 10/1997 |
| WO | WO 97/37720 | 12/1997 |
| WO | WO 98/26840 | 6/1998 |
| WO | WO 98/43700 | 10/1998 |
| WO | WO 98/43701 | 10/1998 |
| WO | WO99 06105 A1 | 2/1999 |
| WO | WO 99/11174 | 3/1999 |
| WO | WO 99/45870 | 9/1999 |
| WO | WO99 49934 A1 | 10/1999 |
| WO | WO 00/25664 | 5/2000 |
| WO | WO 00/25860 | 5/2000 |
| WO | WO 00/25861 | 5/2000 |
| WO | WO 00/25862 | 5/2000 |
| WO | WO 00/25863 | 5/2000 |
| WO | WO00 56677 A1 | 9/2000 |
| WO | WO 02/065895 | 8/2002 |
| WO | WO03 003791 A1 | 1/2003 |
| WO | WO 03/033070 | 4/2003 |
| WO | WO03 033070 A1 | 4/2003 |
| WO | WO 03/041795 A1 | 5/2003 |
| WO | WO03 092807 A1 | 11/2003 |

OTHER PUBLICATIONS

International Search Report, Application No. PCT/US2004/032643, mailed Feb. 14, 2005.

International Search Report, Application No. PCT/US2004/032644, mailed Feb. 14, 2005.

Spencer L. BeMent, Kensall D. Wise, David J. Anderson, Khalil Najafi & Kenneth L. Drake, *Solid-State Electrodes for Multichannel Multiplexed Intracortical Neuronal Recording*, IEEE Transactions On Biomedical Engineering, vol. BME-33, No. 2, Feb. 1986.

Kelly E. Jones & Richard A. Normann, *An Advanced Demultiplexing System for Physiological Stimulation*, IEEE Transactions On Biomedical Engineering, vol. 44, No. 12, Dec. 1997.

Tayfun Akin, Khalil Najafi and Robert M. Bradley, "*A Wireless Implantable Multichannel Digital Neural Recording System for a Micromachined Sieve Electrode*", IEEE Journal of Solid-State Circuits, vol. 33, No. 1, Jan. 1998.

Khalil Najafi and Kensall D. Wise, "*An Implantable Multielectrode Array with On-Chip Signal Processing*", IEEE Journal of Solid-State Circuits, vol. SC-21, No. 6, Dec. 1986.

\* cited by examiner

SYSTEM, APPARATUS AND METHOD FOR INTERACTING WITH A TARGETED TISSUE OF A PATIENT

TECHNICAL FIELD

The present invention generally relates to implantable medical devices, and more particularly relates to a system, apparatus and method for interacting with a targeted tissue of a patient.

BACKGROUND

Implantable medical devices (IMD's) are devices placed inside a body to monitor certain physiological signals and provide or permit therapy to an organ or tissue in response to the physiological signals. Examples of IMD's include heart monitors, therapy delivery devices, pacemakers, implantable pulse generators, pacer-cardio-defibrillators, implantable cardio-defibrillators, cardiomyo-stimulators, nerve stimulators, gastric stimulators, brain stimulators, and drug delivery devices.

In the current state of the art, the sensing and/or stimulation functions of the IMD are controlled from an implantable module, typically housing a power source, a communications means that permits control of the module, such as by telemetry, logic circuitry that controls the functioning of the module independent of inputs via telemetry, and electronics for modulating the inputs and outputs to and from the module. The sensing and/or stimulation functions typically are performed by leads, implanted near a site of interest or the "targeted tissue," that comprise tissue interaction elements, such as stimulation electrodes, drug ports, sensors and sensing electrodes and the like. The tissue interaction elements are in electrical communication with the implantable module via dedicated conductors that extend the distance from the targeted tissue to the implantable module. Typically, each tissue interaction devices is connected to its own dedicated conductor. Each dedicated conductor requires a feedthrough access from the control module, a wire conductor for transmitting electronic signals, means for insulating the wire conductor from the body and from other wire conductors, and means for connecting the wire conductors to the tissue interaction devices. Because the dedicated conductors may extend for relatively long distances, such as, for example, from the abdomen to the spinal cord, the conductors typically are configured to withstand significant tensile and flex demands implied by the long run. The conductors typically also are adapted to minimize energy loss due to impedance. Further, the long conductors should be configured to reduce or eliminate dangerous exposure of the patient to the coupling of energy into the conductors from external alternating magnetic fields in such environments such as magnetic resonance imaging, diathermy, and theft detection. Accordingly, to meet these demands and requirements, the conductors often are sizable.

While it may be advantageous to use ten, twenty, fifty or more tissue interaction devices at a targeted site, the use of this many tissue interaction devices has not been feasible because of the size limitations imposed by the body on the number of sizable conductors that can be implanted, particularly through arterial or venous blood vessels. In addition, the long conductor runs combined with signal-to-noise requirements of certain sensing and/or stimulation systems requires sophisticated design of the leads that house the tissue interaction devices to minimize noise and maximize isolation of the conductors from each other and the surrounding environment.

Accordingly, it is desirable to provide an improved medical system and apparatus for interacting with a tissue of a patient. In addition, it is desirable to provide an improved method for interacting with a tissue of a patient. Furthermore, other desirable features and characteristics of the present invention will become apparent from the subsequent detailed description and the appended claims, taken in conjunction with the accompanying drawings and the foregoing technical field and background.

BRIEF SUMMARY

A method and an apparatus are provided for interacting with targeted tissue of a patient. The apparatus comprises a central control module, a satellite module, and a lead. The central control module is adapted for subcutaneous implantation and is coupled to the satellite module. The satellite module comprises a processor, a communication module, a switching module, a memory, a sense amp, and an A/D converter. The communication module is coupled to the processor for communicating with the central control module. The switching module is coupled to the processor. The memory is coupled to the communication module and the processor. The A/D converter is coupled to the sense amp and the memory. The satellite module is adapted for subcutaneous implantation and is coupled to the lead. The lead is adapted for subcutaneous implantation and has at least one tissue interaction element.

A method of communicating between a central control module and a satellite module for interacting with targeted tissue of a patient is provided. A programming word comprising information to be sent to the satellite module is provided. The programming word is converted into identifiable groups of pulses corresponding to bits of the programming word. The identifiable groups of pulses are sent to the satellite module. The identifiable groups of pulses are converted to information for providing a therapy to the patient. The energy from the identifiable groups of pulses is stored to power the satellite module.

BRIEF DESCRIPTION OF THE DRAWINGS

The present invention will hereinafter be described in conjunction with the following drawing figures, wherein like numerals denote like elements.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Figure 1:
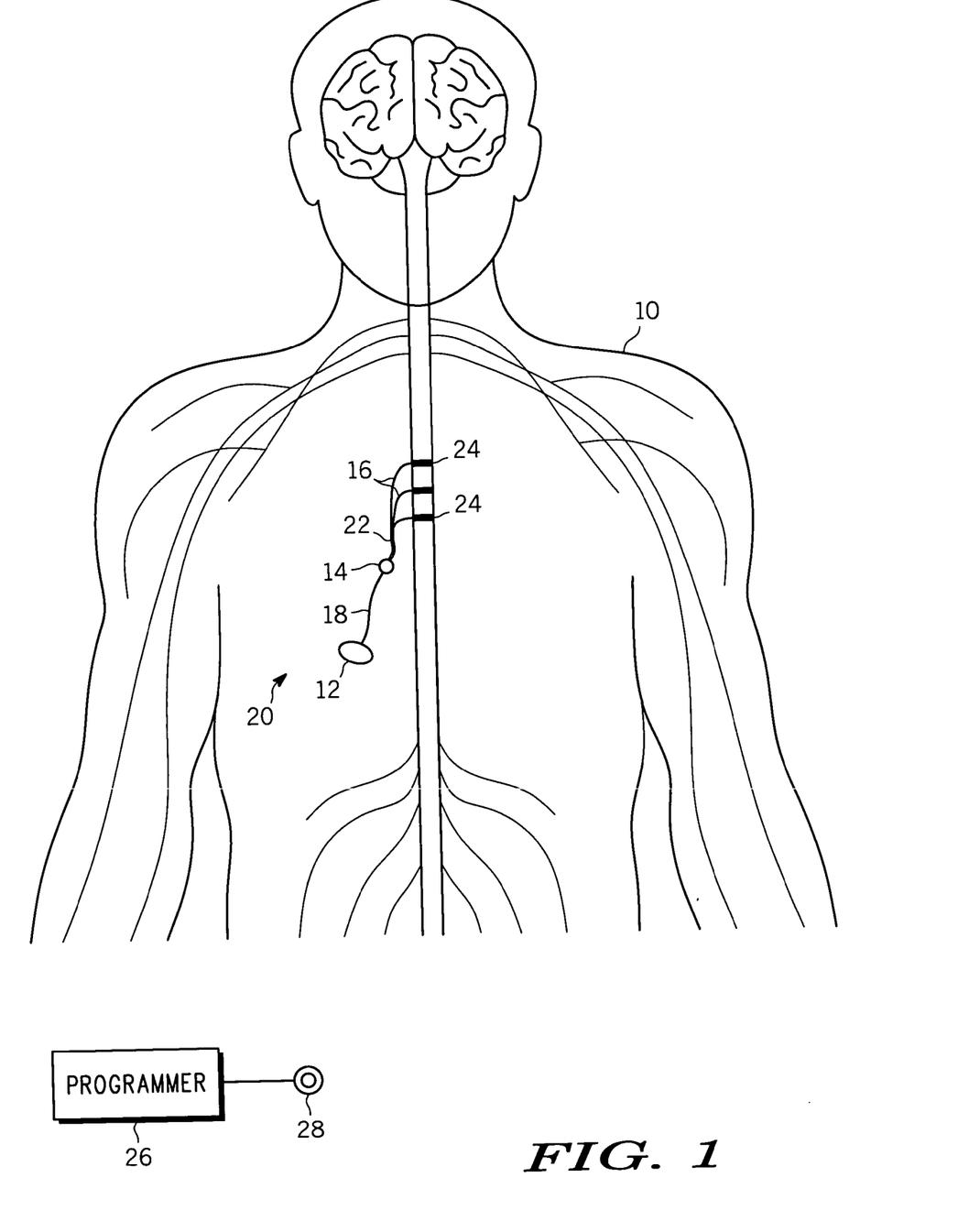
FIG. 1 depicts a system for interacting with a targeted tissue of a patient in accordance with an embodiment of the present invention.

FIG. 1 illustrates an apparatus 20 for interacting with a targeted tissue of a patient 10, in accordance with one exemplary embodiment of the present invention. Apparatus 20 may comprise any suitable sensing or therapy delivery device, such as, for example, a spinal cord stimulation system, a deep brain EEG sensing and stimulation apparatus, a drug delivery therapy device and the like, that is preferably implanted below the skin of patient 10. Apparatus 20 comprises a central control module 12 and at least one satellite control module 14 that is coupled to central control module 12 via one or more first conductors 18. Central control module 12 and satellite control module 14 are both hermetically sealed components that present biocompatible surfaces to the targeted tissue and surrounding tissue. One or more leads 16 are coupled to satellite control module 14 via one or more second conductors 22.

Lead 16 comprises at least one tissue interaction element 24, which can be a stimulation electrode, a recording electrode, a drug delivery device, a sensor, such as a chemical or pressure sensor, or any other type of element or combination of elements configured to interact with a targeted tissue of a patient. As used herein, the term "interact" means sensing physiological signals from a targeted tissue and/or providing a therapy, such as electric stimulation, drugs, and the like to the targeted tissue. Lead 16 may include a paddle lead. Alternatively, lead 16 may comprise any other conventional lead known and used in the medical industry. The location of the tissue interaction element(s) 24 is determined by the type of treatment or monitoring that is desired.

A plurality of satellite control modules 14 and leads 16 also may be employed in the apparatus of the present invention to permit or facilitate acquisition of signals or data from different areas, portion or regions of the body and/or to permit or facilitate the distribution of therapy to different areas, portions or regions of the body. In one embodiment of the present invention, lead 16 comprises one tissue interaction element 24, such as pressure or temperature sensor. In another embodiment of the present invention, lead 16 comprises a plurality or string of like or unlike tissue interaction elements disposed along the length of lead 16 such that each tissue interaction element interacts with tissue at a location in, on or near a portion of the body that is different from that tissue with which an adjoining tissue interaction element interacts. Thus, lead configurations other than those shown explicitly in the Drawings may be practiced in conjunction with the present invention.

Although the invention will be described herein with reference to spinal cord stimulation (SCS) procedures and/or deep brain stimulation (DBS) procedures, it will be understood that the invention finds utility in applications other than SCS and DBS procedures, such as peripheral nerve or ganglia stimulation, intra-spinal stimulation, sacral root stimulation, or intraventricular cerebral stimulation. In addition, the invention may also be utilized to provide stimulation or monitoring of various muscles of the body, such as the cardiac muscle. The invention also finds utility to drug therapy where electrical components are replaced with conduits and catheters for conducting drug material to the therapy site. Furthermore, the invention may also be utilized to monitor physiological signals, such as intracranial fluid pressure or temperature.

Central control module 12 of an SCS apparatus may be programmed to provide a predetermined stimulation dosage in terms of pulse amplitude, pulse width, pulse frequency, or duty cycle to satellite control module 14. In an exemplary embodiment of the present invention, a programmer 26 may be utilized to provide stimulation parameters to central control module 12 via telemetry. Any of a number of suitable programming and telemetry methodologies known in the art may be employed so long as the desired information is transmitted to and from central control module 12. While the components of apparatus 20 typically are implanted subcutaneously, programmer 26 preferably is located outside a patient's body. Accordingly, programmer 26 is coupled to an antenna 28. Alternatively, central control module 12 and programmer 26 may exchange data or information by any other suitable means, such as electrical, telemetric, radio, infrared, or other means well known to those skilled in the art.

Figure 2:
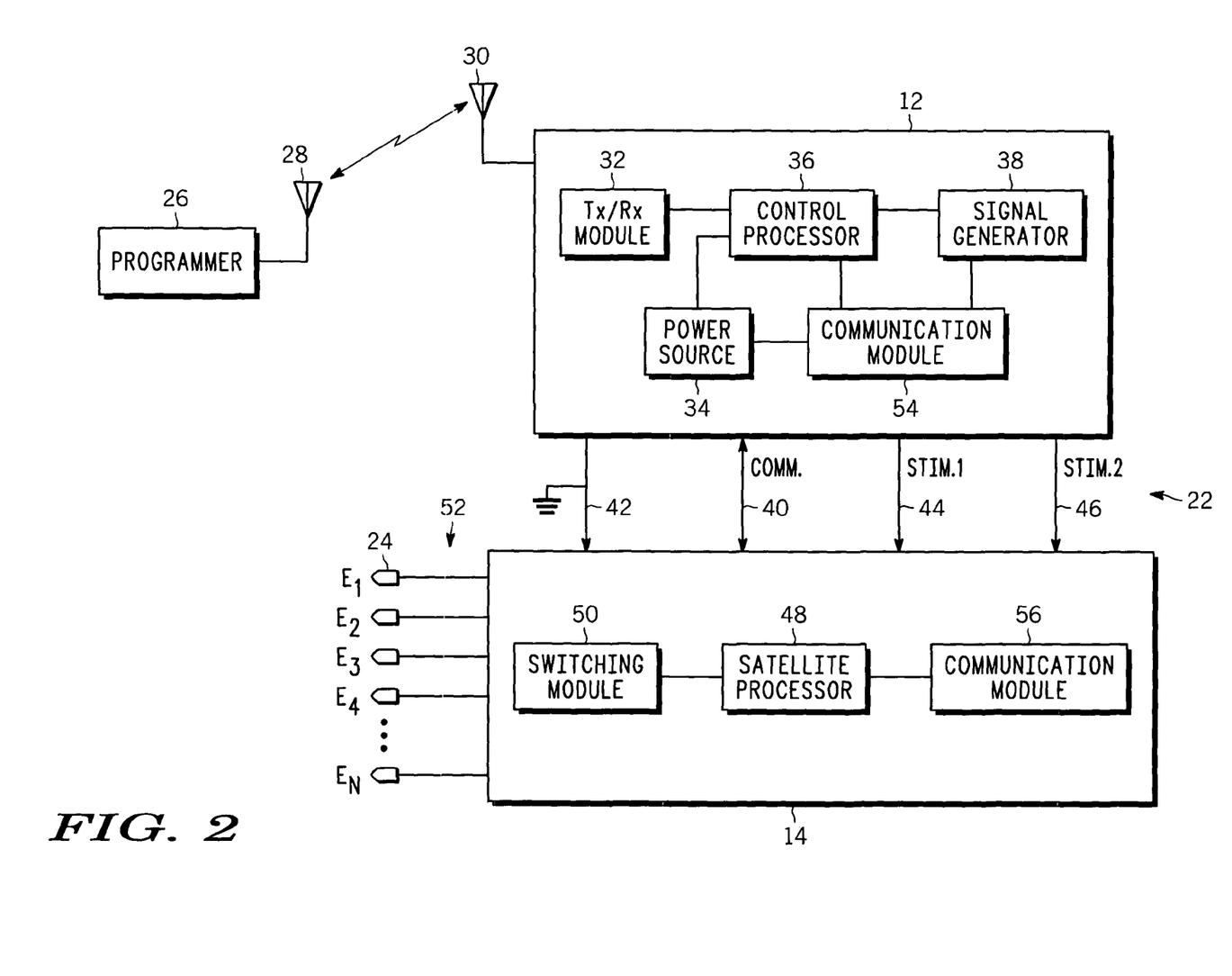
FIG. 2 is a block diagram of the system illustrated in FIG. 1.

FIG. 2 illustrates an exemplary embodiment of the apparatus of the present invention comprising central control module 12, which is implanted in a patient's stomach, satellite control module 14, which is implanted in or proximate to the spinal cord, and a plurality of tissue interaction elements 24, which in this embodiment are electrodes that are implanted within or proximate to the targeted tissue of the spinal cord. The functionality and features of central control module 12 may vary in sophistication, ranging between simple (e.g., merely providing power to the tissue interaction elements 24 and relaying information gathered therefrom to programmer 26) to complex (e.g., processing and/or storage of acquired signals by a microprocessor, controller, digital signal processor or other computing device, determining whether a predetermined condition or state exists in the patient, triggering a therapy in response to detecting such a condition or state). Similarly, the sophistication of the functionality and features of satellite control module 14 may range between simple (e.g., merely acting as a switching mechanism for tissue interaction elements 24) to very complex (e.g., acquiring, processing, and/or storing signals from the tissue interaction elements, determining whether a predetermined condition or state exists in the patient, triggering a therapy in response to detecting such a condition or state).

Further, the functionality and features of apparatus 20 may be divided between central control module 12 and satellite control module 14, depending on such factors as the size of the various components required for performing desired functions and the type and timing of treatment required to be provided by the tissue interaction elements 24. Accordingly, in one embodiment of the present invention, bulky components that consume relatively large amounts of real estate may be located in the central control module, which may be positioned remote from the targeted tissue and small components that consume relatively small amounts of real estate may be located in the satellite control module, which may be positioned close to or in the targeted tissue. In another embodiment of the present invention, if sensing of the targeted tissue with relatively instantaneous treatment of the tissue based on signals sensed is required, components that perform sensing, data or signal processing and therapy delivery may be located on the satellite control module. By locating in the satellite control module certain functionality and features that in the prior art typically are performed by the central control module, the number and size of connectors between central control module 12 and satellite control module 14 can be minimized. Further, because they run only a relatively limited distance between satellite control module 14 and tissue interaction elements 24, the wire connectors between satellite control module 14 and tissue interaction elements 24 can be formed of finer materials and comprise small geometries that may permit the use of a denser concentration of tissue interaction elements 24 at the targeted tissue.

Referring to FIG. 2, where apparatus 20 may comprise an SCS system, central control module 12 is coupled to programmer 26, preferably via antennae 28 and 30. Thus, central control module 12 may comprise a transreceiver module 32 that controls the delivery to and receipt from programmer 26 of information and data. Central control module 12 preferably comprises a suitable implantable source of electrical energy (power source) 34 to power satellite control module 14, leads 16, and the circuitry of central control module 12. In one embodiment of the invention, power source 34 may be any suitable source of electrical energy in accordance with common practice in the art, and may be any one of a primary battery, a secondary battery, a capacitor, and the like. Central control module 12 also comprises a control processor 36. Control processor 36 may comprise a microprocessor, microcomputer, or other micro-controller, controller or digital signal processor. Control processor 36 is configured to select and power tissue interaction elements 24, control the circuitry of central control module 12, and may also be adapted to receive, process and store signals from satellite control module 16. Central control module 12 further comprises a signal generator 38 that is controlled by control processor 36 and is configured to send to satellite control module 16 stimulation signals that will be distributed to the targeted tissue by electrodes 24. Central control module 12 further may comprise a communications module 54 that is responsible for transmitting instructions and data received by central control module 12 from programmer 26 to satellite control module 14 and for receiving signals and data transmitted from satellite control module 14 and forwarding them to the appropriate component for processing or transmitting to programmer 26.

Central control module 12 is coupled to satellite control module 16 by conductor 22, which in this embodiment comprises a communications connector 40 and ground connector 42 that serve to supply power and information to satellite control module 16. Power may be delivered from central control module 12 to satellite control module 16 along communications connector 40 via an AC or pulsed DC power delivery method that has digital communication signals interleaved or superimposed on the power signal. If the power delivered along communications connector 40 is not sufficient to power the circuits of satellite control module 16 and to deliver stimulation energy to the electrodes 24, then one or more additional connectors, such as stimulation connectors 44 and 46, may be utilized to deliver stimulation signals to satellite control module 16. As illustrated in FIG. 2, stimulation connector 44 may deliver to satellite control module 16 a signal, STIM. 1, having a first voltage level and stimulation connector 46 may deliver to satellite control module 16 a signal, STIM. 2, having a second voltage level. Central control module 12 is a power source and a communication hub between programmer 26 and satellite module 14. This allows the bulky components of the system to be placed in a convenient area of the patient. Preferably, conductor 22 comprises as few connectors as possible to transmit the desired power and stimulation signals. In this manner, only a limited number of connectors may be used to run the full distance between central control module 12 and the satellite control module 14 and, thus only this limited number of connectors may be adapted to withstand the full tensile and flex demands implied by the relatively long run between the abdomen and the spinal cord and to minimize noise and signal reduction. In an alternative embodiment of the present invention, different therapy stimulation signals may be delivered to the electrodes by using the central control module 12 to transmit a single signal to the satellite control module 14 and by using the satellite control module 14 to modulate the signal to the desired therapy stimulation levels.

Satellite control module 14 comprises a communications module 56, a processor 48 and a switching module 50. Satellite control module 14 locally controls a treatment methodology being applied to the patient. In other words, interaction with electrodes 24 is determined within satellite module 14 based on the programming stored therein. Data and programming information is channeled back and forth through control module 12 to satellite module 14. Communications module 56 is adapted to communicate with communications module 54 of central control module 12. Satellite processor 48 may comprise a microprocessor, microcomputer, or other micro-controller, controller or digital signal processor. Processor 48 is responsible for receiving and processing instructions and information from central control module 12 via communications module 56 and controls switching module 50 that distributes and polarizes the signals received from central control module 12.

Satellite control module 14 is coupled to electrodes 24 via dedicated electrode connectors 52. Typically, satellite control module 14 is implanted in a patient at a location proximate to the site or sites of electrodes 24. Accordingly, by positioning the electrode switching, powering and polarizing functions at the satellite control module 14, the dedicated electrode connectors 52 may have smaller geometries than if they were required to extend the distance between electrodes 24 and central control module 12. Thus, a larger number of electrodes 24 may be utilized at the targeted tissue. In addition, because the run of dedicated electrode connectors 52 can be reduced, a reduction of signal loss and attention along dedicated electrode connectors 52 may result.

Figure 3:
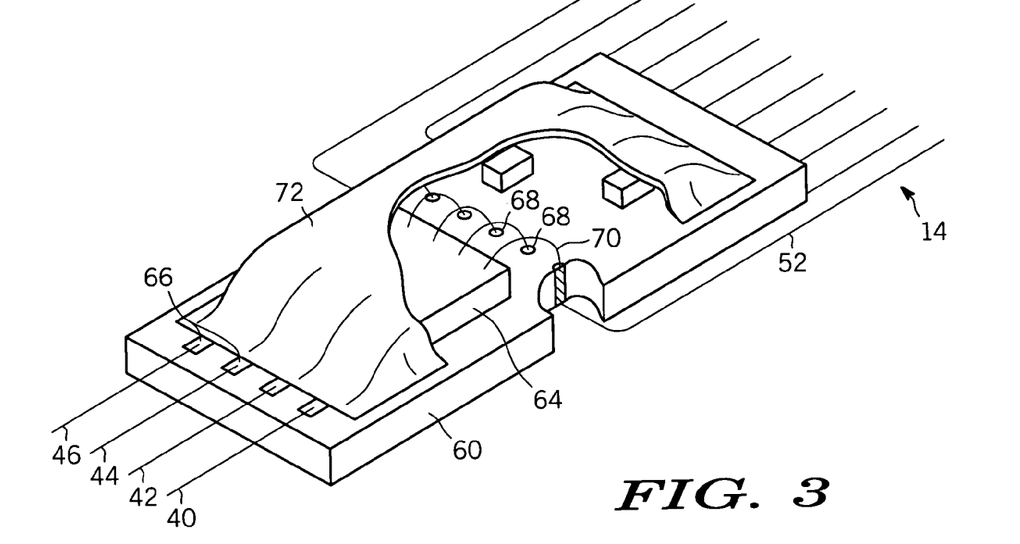
FIG. 3 is a cut-away view of a satellite control module in accordance with an embodiment of the present invention.

FIG. 3 is a cutaway view of an exemplary embodiment of the satellite control module 14 of the present invention. Satellite control module 14 may comprise a ceramic hybrid circuit substrate 60, which supports the circuitry of the various components of module 14, including processor 48, communications module 56, switching module 50 and any additional circuitry. Satellite control module 14 preferably includes an IC chip 64 which is mounted to one surface of substrate 60 and is connected to electrical traces 66 by, for example, wire bonding. The electrical traces 66 in turn are attached to wire connectors, such as connectors 40, 42, 44 and 46, to couple satellite control module 14 to central control module 12 (not shown). The electrodes (not shown) are coupled to satellite control module 14 via dedicated electrode connectors 52, which are connected to metal-filled vias 68 that, in turn, are coupled to IC chip 64 by wire bonds 70. It will be appreciated that any number of methods could be used to connect IC chip 64 to dedicated electrode conneceters 52 and/or connectors 40-46. For example, in one exemplary embodiment, IC chip 64 can be a flip chip that is coupled to the connectors by metal lines formed on or within substrate 60. The components of satellite control module 14 are hermetically sealed from the environment using metallic cover 72, which may be soldered to substrate 60 but may be separated from electrical traces 66 by, for example, a dielectric coating so that metallic cover 72 and the solder do not short traces 66. It will be understood that any other method for achieving the hermetic seal may be used, such as welding, brazing and the like. In an alternative embodiment of the invention, components of satellite control module 14, such as IC chip 64, may be connected to metallic cover 72. External connections then can be made to metallic cover 72 to communicate with the components of module 14. Other means known in the art also may be used to send signals to or receive signals from the components of satellite control module 14. For example, mutual inductance may be used with a coil patterned on the outside of ceramic network 60 and a coil patterned on the inside of ceramic network 60. Alternatively, capacitive coupling may be used with a capacitive plate positioned on the outside of ceramic network 60 and a capacitive plate positioned on the inside of ceramic network 60. In another embodiment of the invention, antennae may be used to transmit signals across ceramic network 60.

It will be understood that the communication protocol and means used to couple satellite control module 14 and central control module 12 may comprise an independent digital communications means and an independent AC power circuit means located in one or both the central and satellite control modules. Alternatively, central control module 12 may comprise a conventional neuro or cardiac stimulation device that has been modified so that communication signals from the central control module could be generated by the stimulation engine electronics of that device. In this latter approach, central control module 12 could be programmed by programmer 26 to induce the stimulation engine electronics to issue sequences of pulses on a chosen conductor that would be interpreted as 1's and 0's by the satellite control module. Satellite control module 14 then could process the pulses to decipher the communications. In turn, satellite control module 14 may communicate with the central control module 12 by any number of means already existing on central control module 12. For example, confirmation and error check responses from satellite control module 14 could be received by central control module 12 by holding a conductor, such as conductor 40, at a designated impedance level that could be sensed by existing impedance sensing electronics on central control module 12. Alternatively, a designated voltage level that could be sensed by existing voltage sensing electronics or other existing sensing electronics on central control module 12, such as sense amp circuitry in cardiac pacemakers, could be maintained on conductor 40.

Figure 4:
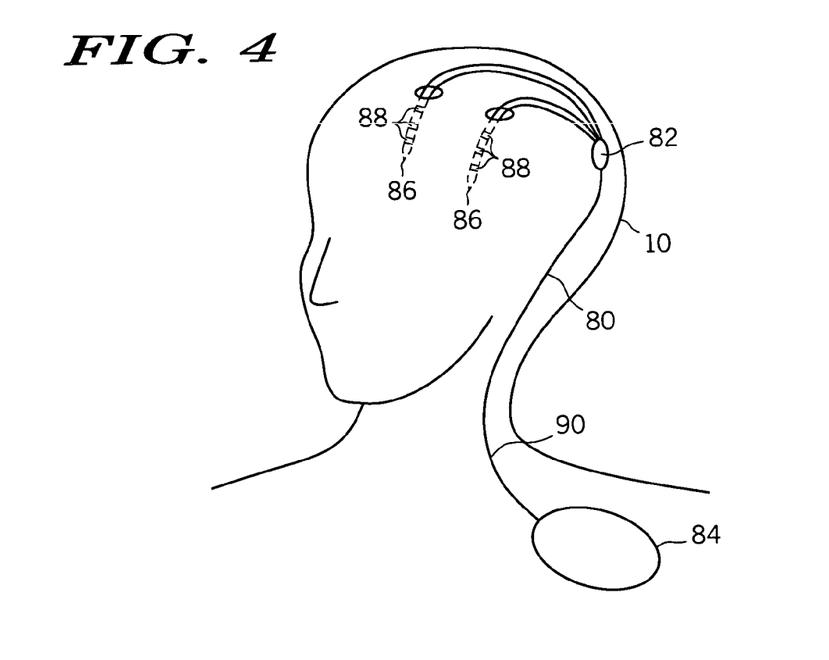
FIG. 4 depicts a system for interacting with a targeted tissue of a patient in accordance with another embodiment of the present invention.

Referring to FIG. 4, in another exemplary embodiment of the invention, a system of the present invention may comprise a deep brain EEG sensing and stimulation system for the detection and termination of epileptic seizures. In this embodiment, an apparatus 80 utilizes a central control module 84 that is implanted proximate to the clavicle of a patient 10. Apparatus 80 further comprises a more sophisticated satellite control module 82, which is implanted within or near the skull and is coupled to central control module 84 by a conductor 90. One or more deep brain stimulation leads 86 having a plurality of tissue interface elements, which in this embodiment are sensing and stimulation electrodes 88, are electrically coupled to satellite control module 82 and are inserted into or proximate to targeted tissue of the brain.

Figure 5:
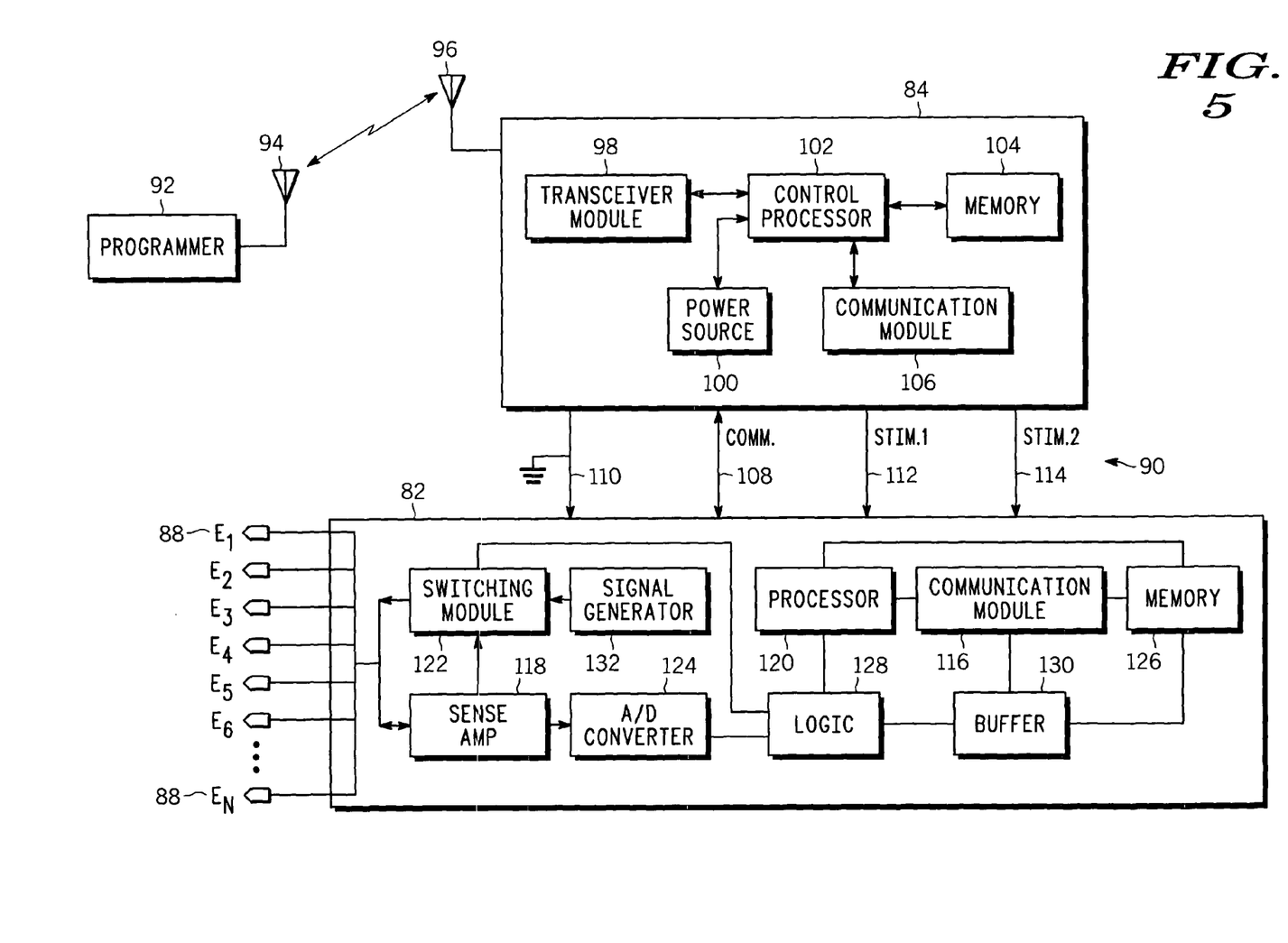
FIG. 5 is a block diagram of the system illustrated in FIG. 4.

Referring to FIG. 5, central control module 84 is coupled to a programmer 92, preferably via antennae 94 and 96. Thus, central control module 84 may comprise a transreceiver module 98 that controls the delivery to and receipt from programmer 92 of information and data. Central control module 84 preferably comprises a suitable implantable source of electrical energy (power source) 100 to power satellite control module 82, leads 86, and the circuitry of central control module 84. In one embodiment of the invention, power source 100 may be any suitable source of electrical energy in accordance with common practice in the art, and may be any one of a primary battery, a secondary battery, a capacitor, and the like. Central control module 84 also comprises a control processor 102. Control processor 102 may comprise a microprocessor, microcomputer, controller or digital signal processor. Control processor 102 may be adapted to control the circuitry of central control module 84 and to receive and process signals from satellite control module 82 and instructions from programmer 92. Signals received from electrodes 88 and instructions and signals received from programmer 92 may be stored in a memory 104. Central control module 84 further may comprise a communications module 106 that is responsible for transmitting instructions and data received by central control module 84 from programmer 92 to satellite control module 82 and for receiving signals and data transmitted from satellite control module 82 and forwarding them to the appropriate component for processing or transmitting to programmer 92. In general, central control module 84 is a power source and a communication hub for the system.

Central control module 84 is coupled to satellite control module 82 by conductor 90, which in this embodiment comprises a communications connector 108 and ground connector 110 that serve to supply power and information to satellite control module 82. Power may be delivered from central control module 84 to satellite control module 82 along connector 108 via an AC or pulsed DC power delivery method that has digital communication signals interleaved or superimposed on the power signal. If the power delivered along connector 108 is not sufficient to power the circuits of satellite control module 82 and to power and deliver stimulation energy to the electrodes 88, then one or more additional connectors, such as stimulation connectors 112 and 114, may be utilized to deliver stimulation signals to satellite control module 82. As illustrated in FIG. 5, stimulation connector 112 may deliver to satellite control module 82 a signal, STIM. 1, having a first voltage level and stimulation connector 114 may deliver to satellite control module 82 a signal, STIM. 2, having a second voltage level. It will be appreciated that any number of additional connectors may be used to deliver desired therapy stimulation signals simultaneously to satellite control module 82. However, preferably, conductor 90 comprises as few connectors as possible to transmit the desired power and stimulation signals. In this manner, only a limited number of connectors may be used to run the full distance between central control module 84 and the satellite control module 82 and, thus only this limited number of connectors may be adapted to withstand the full tensile and flex demands implied by the relatively long run between the clavicle and the skull and to minimize noise and signal reduction. In an alternative embodiment, different therapy stimulation signals may be delivered to the electrodes by using the satellite control module 82 to modulate a signal to the desired therapy stimulation levels.

Satellite control module 82 comprises a communication module 116 that is adapted to receive power, signals and data transmitted from central control module 84 and also is adapted to transmit signals and data to communication module 106 of central control module 84. Satellite control module 84 controls the therapy provided to the patient under normal operation. Local interaction allows for better control and faster response times to the patient. Signals and data received from central control module 84 may be stored and/or processed using satellite processor 120, logic module 128 and buffer 130. Satellite control module 82 also comprises a sense amp 118 adapted for amplifying signals received from electrodes 88 for use in subsequent digital signal analysis, storage and/or data transfer or telemetry. Signals from electrodes 88 may be converted to multi-bit digital signals by A/D converter 124 for storage using buffer 130 and memory 126. Processor 120 or another micro-controller, controller or digital signal processor may employ digital signal analysis techniques to characterize the digitized signals stored in memory 126. Alternatively this characterization may be performed by logic 128. Satellite control module 82 also may comprise a signal generator 132 that generates the therapy stimulation signals that are distributed by the electrodes to the targeted tissue. Selection of the electrodes for sensing and/or stimulation preferably is controlled by processor 120 via switching module 122, which selections may be varied as desired. In another exemplary embodiment of the present invention, satellite control module 82 may also have a power supply (not shown), which may be configured to power electrodes 88 and/or power the circuitry of satellite control module 82.

Satellite control module 82 may be coupled to electrodes 88 via dedicated electrode connectors (not shown) that may extend through leads 86. Preferably, satellite control module 82 is implanted in a patient at a location proximate to the site or sites of implantation of leads 86. Accordingly, by positioning the sensing circuitry and the electrode switching, powering and polarizing functions at satellite control module 82, the dedicated electrode connectors may have smaller geometries than if they were required to extend the distance between electrodes 88 and central control module 84. Thus, a larger number of electrodes 88 may be utilized at the targeted tissue. In addition, the run of the dedicated electrode connectors can be reduced, thus a reduction of signal loss and attention along the electrode connectors can be realized. Further, signal processing at satellite control module 82 permits direct action of the software algorithms supplied by programmer 92 on the analog signal received from electrodes 88, eliminating the need for high-speed digital communication between satellite module 82 and central control module 84 to achieve the same result. Locating the signal processing at the satellite module also may reduce the risk to the patient from the coupling of energy from external alternating magnetic fields.

It will be appreciated that satellite control module 82, electrodes 88, and the dedicated electrode connectors can take on any number of suitable forms. For example, in one embodiment of the invention, satellite control module 82 may be a stand-along device located at a position remote from electrodes 88. While remote from electrodes 88, preferably satellite control module 82 is positioned proximate to electrodes 99 so as to minimize the dedicated electrode connectors that couple module 82 and the electrodes 88. In an alternative embodiment of the invention, satellite control module 82 may be integrated on the same structure or lead as electrodes 88, such as configured on a paddle lead. In this embodiment, satellite control module 82 may be on the same structure as but positioned at a different site on the structure from electrodes 88, thus minimizing the length of the dedicated electrode connectors. Alternatively, satellite control module 82 may be positioned among the electrodes 88, thus further minimizing the length of the dedicated electrode connectors.

With the above described system illustrated in FIGS. 4 and 5, if satellite control module 82 detected an EEG event of interest, the analog EEG signals from electrodes 88 could be converted to a digital signal via A/D converter 124. Buffer 130 and memory 126 could be used to store the selected digitized waveform, which then could be sent to central control module 84 at a clocking rate that corresponds with the capability of the serial digital link between the two modules. Alternatively, the analog signals could be transmitted from satellite control module 82 to central control module 84 in analog form and the analog signals could be converted to digital form at the central control module for further processing or transmissions to programmer 92. Satellite control module 82 also could be configured to send only status and alert signals (indicating, for example, that onset of seizure is detected or is not detected) to the central control module 84 as determined by default settings in the satellite control module 82 and/or the central control module 84 or as determined in accordance with instructions programmed by a physician.

Using an embodiment of the system of the present invention illustrated in FIGS. 4 and 5, a physician could verify placement of the leads and could adjust stimulation sites by using user interface software of programmer 92 to uplink to central control module 84 instructions to address certain electrodes positioned on the distal end of the leads. Preferably, each electrode has its own address that could be individually designated. The physician's instructions could be transmitted telemetrically from programmer 92 to central control module 84, which could process the instructions into signals that could be understood by satellite control module 82. Upon receipt of the signals, satellite control module 82 may generate stimulation signals and transmit the stimulation signals to a designated electrode. Accordingly, any mechanical movement of the leads after placement, which may be caused by, for example, suturing the wound, locking the lead into a burr-hole cap, or other disturbances caused during or after surgery, could be corrected at a time after placement of the leads through commands from programmer 92, which can be programmed to change the combination of the stimulating and sensing electrodes so that desired positions in the brain can be targeted. In addition, a physician can program numerous electrodes spaced from each other to sense and/or stimulate multiple targeted sites of the brain.

It is also contemplated in the present invention that appropriate therapy can be delivered to the brain by the system in response to a predetermined condition or state, such as detection of the onset of a seizure. For example, a system of the present invention comprising programmer 92, central control module 84, satellite control module 82 and one or more stimulation and sensing electrodes 88 implanted within or near the targeted tissue of the brain and connected to satellite control module 82, is preferably capable, upon detecting or sensing the presence of a predetermined intracranial condition or state (such as electronic pulses indicative of the onset of a seizure), of having satellite control module 82, central control module 84, programmer 92 and/or other external device provide or deliver an appropriate therapy. The appropriate therapy may be delivered to that region of the brain where therapy should optimally be provided in response to such predetermine conditions being detected, such as by transmitting regulating stimulation signals to the brain to prevent a seizure. Alternatively, the system may be configured to provide one or more other therapies in place of or simultaneously with the transmission of electronic signals, such as, for example, the delivery of drugs to the patient.

In accordance with one exemplary embodiment, the system of the present invention may be utilized in a patient according to the following method. At least one tissue interaction element is implanted in a patient on or proximate to a targeted tissue. The tissue interaction element may be coupled to a satellite control module, which is implanted in the patient at a location preferably proximate to the tissue to be targeted by the tissue interaction element. The tissue interaction element may be coupled to the satellite control module via a dedicated connector, the physical dimensions of which may be reduced by minimizing the distance between the satellite control module and the tissue interaction device. The satellite control module may be coupled to a central control module, which is implanted in the patient at a location remote from the satellite control module. The satellite control module may be coupled to the satellite control module by one or more conductors or connectors. Preferably, the conductors or connectors are adapted to withstand the tensile and flex demands that are implied from the run between the satellite control module and the central con troll module. The tissue interaction element then may be caused to interact with the targeted tissue by activation of ht central control module. It will be appreciated that the tissue interaction element(s), satellite control module and central control module may be implanted in the body, in any order, with the respective coupling connections made during or after implantation of the appropriate devices.

Figure 6:
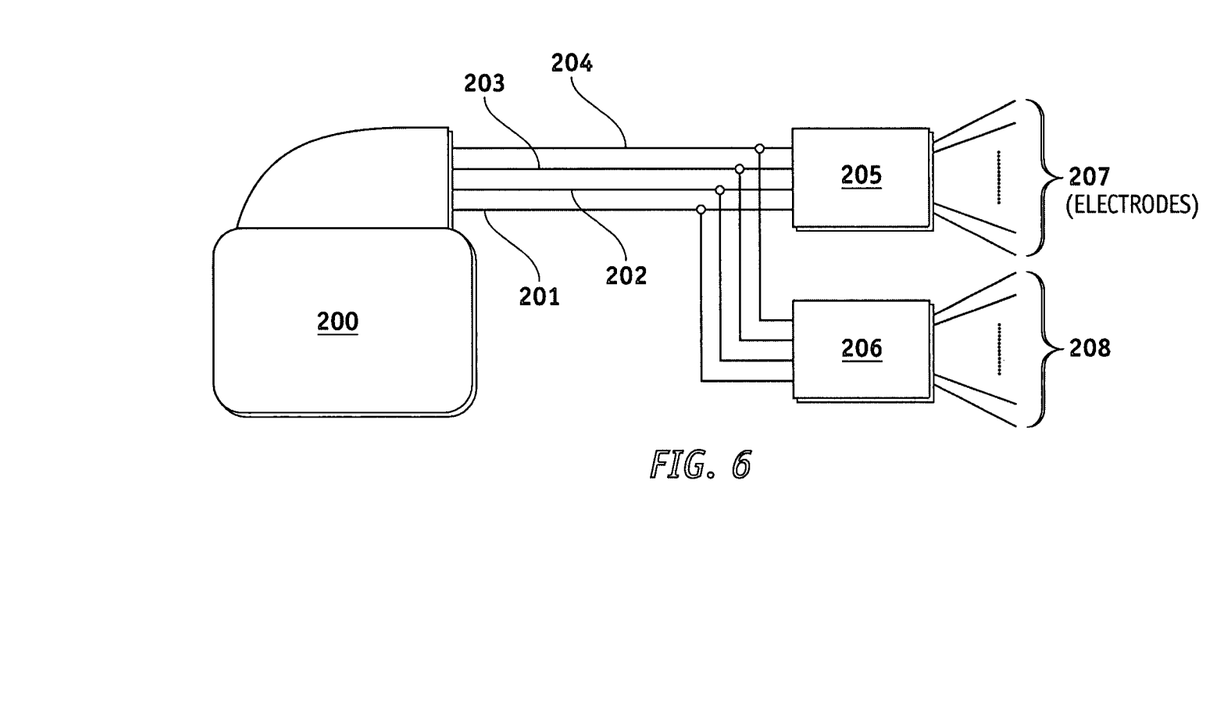
FIG. 6 is a block diagram of a central control module coupled to two satellite modules in accordance with the present invention.

FIG. 6 is a block diagram of a central control module 200 coupled to two satellite modules in accordance with the present invention. Central control module 200 is coupled to a satellite module 205 and a satellite module 206 by wires 201, 202, 203, and 204. In an embodiment of the system, wires 201 and 202 are respectively power and ground wires. Wires 203 and 204 are respectively a channel 1 and a channel 2 of the system for providing stimulus to drive the electrodes. In an alternate embodiment, only wires 201 and 202 are required for providing power and stimulus. In either case, wiring between central control module 200 and satellite modules 205 and 206 is kept to a minimum.

Satellite module 205 couples to electrodes 207. Similarly, satellite module 206 couples to electrodes 208. Electrodes 207 and 208 are placed on targeted tissue of a patient to provide a therapy. Satellite modules 205 and 206 are placed as close as possible to the targeted tissue. Ideally, satellite modules 205 and 206 are dimensionally small allowing the proximal placement to the targeted tissue. Placing satellite modules 205 and 206 in proximity to the targeted tissue relaxes the electrical interconnection and physical dimension requirements, for example wire diameter, thus allowing the number of electrodes used to be substantially increased. In an embodiment of the system, satellite modules 205 or 206 are not enabled simultaneously but are selectively enabled to provide therapy to their corresponding targeted tissue.

Satellite modules 205 and 206 are powered by voltage pulses provided by central control module 200. The voltage pulses are also arranged in a manner to communicate with satellite modules 205 and 206. In general, the information being sent first takes the form of one or more programming words. For example, the programming word can be generated by a programmer external to the patient. The programming word is sent by radio frequency signal to central control module 200. The programming word is then converted by central control module 200 to groups of pulses that are applied to wire 201. The groups of pulses are sent in a manner that they can be received and converted by the appropriate satellite module such that the information is retrieved.

As mentioned previously, the groups of pulses sent on wire 201 have a dual purpose, besides communication, they power satellite modules 205 and 206. The energy from the pulses is stored, for example on a capacitor to power satellite modules 205 and 206. Thus, the communication methodology requires that sufficient pulses are continuously sent to ensure stable power to satellite modules 205 and 206 under all operating conditions. Central control module 200 provides pulses even when no communication is occurring to power satellite modules 205 and 206. An efficient communication methodology may supply enough power to satellite modules 205 and 206 making wires 203 and 204 unneeded. In this case, satellite modules 205 and 206 would generate stimulation signals internally to drive electrodes 207 and 208. Alternately, as shown, wires 203 and 204 are added to provide different stimulus thereby increasing the flexibility of the therapy that can be provided and also reducing the burden for power transfer on wire 201. Limiting interconnection between central core module 200 and satellite modules 205 and 206 to four or less wires reduces problems associated with long wire runs subcutaneously placed in the patient.

An example of an operating sequence illustrates the flexibility of the system to cope with the needs of the patient. Electrodes 207 are enabled to sense activity at the targeted tissue of the patient. A signal received by an electrode is an analog signal. The analog signals are received by satellite module 20, amplified, converted by an analog to digital converter, and stored in memory. Conversion of the analog signals allows multiple signals to be received from several electrodes of electrodes 207 and processed at a later time. Digital conversion is beneficial for processing and the transmission of the information. Satellite modules 205 and 206 are capable of controlling and providing a therapy to the targeted tissue. The information received from electrodes 207 is analyzed in satellite module 205 and an appropriate therapy is implemented by satellite module 205.

Another option is to send the information to central control module 200. The information is then sent to a programmer external to the patient by radio frequency transmission from central control module 200. The programmer also analyzes the information and develops a modification to the therapy based on substantially more treatment data available externally. The programmer transmits the modified therapy by radio frequency transmission to central control module 200. Central control module 200 then sends the modification to the therapy to satellite module 205. The modification to the therapy is stored in memory and implemented by satellite module 205. Thus, local response can be made very rapidly by satellite modules 205 and 206 having the capability to detect, analyze, and implement therapies for the patient. Alternatively, the information can be transferred to central control module 200 or an external programmer for more analysis.

Figure 7:
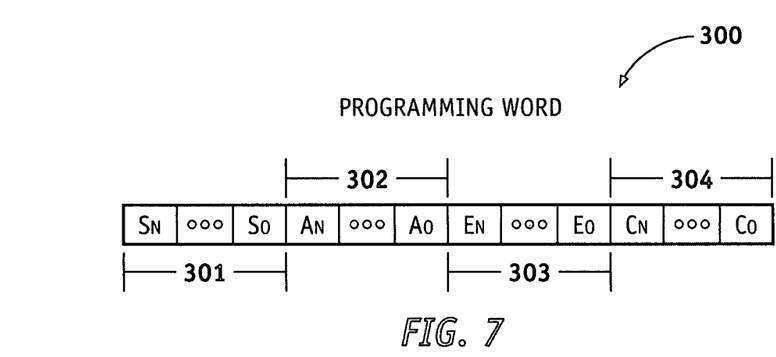
FIG. 7 is an example of a programming word in accordance with the present invention.

FIG. 7 is an example of a programming word 300 in accordance with the present invention. In general, programming word 300 has a fixed number of bits that is selected to provide the information required. An example is provided to illustrate how programming word 300 carries information. Programming word 300 comprises four sections of bits dedicated for different functions in communicating information from central control module 200 to satellite modules 205 and 206 of FIG. 6 (or vice versa). A section 301 contains the start bits $S_n$ to $S_0$ that identify the beginning of programming word 300. A section 302 of programming word 300 contains the satellite module address $A_n$ to $A_0$ that identifies which satellite module (205, 206) receives the information. For example if only satellite modules 205 and 206 were coupled to central control module 200 a single module address bit would be required to distinguish between the two. A section 303 of programming word 300 contains the electrode settings $E_n$ to $E_0$ on how each electrode is set. In an embodiment of the system as shown in FIG. 6, each electrode has four possible states. Two bits are required to identify the state of each electrode. For example, an electrode is in a floating state when the corresponding bits of programming word 300 are in a 00 state. The electrode is a cathode when the corresponding bits of programming word 300 are in a 01 state. The electrode is coupled to channel 1 when the corresponding bits of programming word 300 are in a 10 state. Finally, the electrode is coupled to channel 2 when the corresponding bits of programming word 300 are in a 11 state. Thus, if there are 20 electrodes coupled to each of satellite modules 205 and 206, forty bits would be required in section 303 with each electrode having two of the forty bits to identify its state. Finally, section 304 contains the cyclic redundancy code $C_n$ to $C_0$ corresponding to the information being sent. The cyclic redundancy code is used to check if the programmable word was sent correctly. In general, a polynomial is applied to the block of data being sent which generates the cyclic redundancy code. The receiving entity similarly applies the polynomial to the block of data received and compares the generated code to the appended cyclic redundancy code sent on the block of data. The data is correct if the codes match. Conversely, non-matching codes indicates an error in transmission.

A conversion process of programming word 300 is implemented to send information on wire 201. Programming word 300 is converted by central control module 200 into groups of pulses that can be identified by satellite modules 205 and 206. In an embodiment of the system, programming word 300 is read X bits at a time. The X bits are converted to a corresponding decimal number. A number of pulses equal to the corresponding decimal number is output by central control module 200 followed by a predetermined delay. The next X bits of programming word 300 are then read and converted to a number of pulses followed by the predetermined delay. This is repeated until all the bits are read. To illustrate this methodology assume that three bits are read and 1 is added to the three bits to determine the number of pulses read out. An example of a programming word is a sequence of bits 111110001010011110001. Breaking this sequence of bits into groups of three yields 111, 110, 001, 010, 011, 110, 001. Converting each of the these groups of three bits to decimal and adding one yields the following decimal sequence, 8, 7, 2, 3, 4, 7, 2. Thus, central control module 200 would output a sequence of 8 pulses, 7 pulses, 2 pulses, 3 pulses, 4 pulses, 7 pulses, and 2 pulses. In one embodiment, the pulse sequences would then be converted back to the programming word and the information contained therein utilized by the satellite module. This methodology is for illustrative purposes and should be appreciated that a wide range of variations fall within this scheme such that sufficient pulses are provided to power the satellite modules.

While at least one exemplary embodiment has been presented in the foregoing detailed description, it should be appreciated that a vast number of variations exist. For example, while the present invention has been described with reference to a spinal cord stimulation system and a deep brain stimulation system, it will be understood that the present invention finds utility in other sensing and/or stimulation and/or therapy delivery systems. In addition, while the present invention has been described using electrodes as the tissue interaction elements, it will be understood that any variety of sensors, stimulators, therapy delivery devices and the like may be utilized. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A system for interacting with targeted tissue of a patient and for use in conjunction with a remote programmer and a power source, the system comprising:
  a central control module adapted for subcutaneous implantation, the central control module comprising;
    a housing configured to house the power source; and
    a wireless receiver disposed in said housing, the wireless receiver configured to be coupled to the power source and to receive programming signals from the remote programmer;
  a first lead coupled to the central control module that comprises at least one connector, the first lead carrying power from the power source and digital communications including the programming signals from the wireless receiver, the power and the digital communications being combined on the at least one connector;
  a satellite module adapted for subcutaneous implantation coupled to said central control module by means of said first lead, said satellite module comprising:
    a processor coupled to said wireless receiver by the first lead and configured to be coupled to the power source by the first lead;
    a communication module coupled to said processor for coupling the processor to the wireless receiver by communicating with said central control module by the first lead;
    a switching module coupled to said processor;
    a memory coupled to said communication module and said processor;
    a signal generator coupled to the switching module;
    a sense amp; and
    an A/D converter coupled to said sense amp and said memory; and
  a plurality of second leads adapted for subcutaneous implantation coupled to said sense amp and said switching module, each of said second leads having at least one tissue interaction element,
  wherein said processor is configured to receive said programming signals from said wireless receiver over the first lead, to control the signal generator to generate stimulation signals, and to control said switching module to selectively distribute the generated stimulation signals or receive sensed signals to or from the plurality of second leads.

2. The system for interacting with targeted tissue of a patient as recited in claim 1 wherein the central control module further includes a communication module coupled to the power source and the satellite module.

3. The system for interacting with targeted tissue of a patient as recited in claim 2 wherein the central control module is limited to providing power to the satellite module and acting as a communication hub of the system.

4. The system for interacting with targeted tissue of a patient as recited in claim 1 wherein the satellite module further includes:
  a logic block coupled to the switching module; and
  a buffer coupled to the logic block and the memory.

5. The system for interacting with targeted tissue of a patient as recited in claim 1 wherein the central control module and satellite module is limited to two wire interconnections for providing power and communication.

6. The system for interacting with targeted tissue of a patient as recited in claim 1 wherein the central control module and satellite module is limited to four wire interconnections for providing power, communication, and stimulation signals.

7. The system for interacting with targeted tissue of a patient as recited in claim 1 wherein control of a therapy stimulation signals to the targeted tissue of a patient is controlled by the satellite module.

8. The system of claim 1, wherein the power and the digital communications are combined on the at least one connector by the digital communications being superimposed on the power.

9. The system of claim 1, wherein the power and the digital communications are combined on the at least one connector by the digital communications being interleaved with the power.

\* \* \* \* \*